United States Patent
Hurtubise

(10) Patent No.: US 11,713,434 B2
(45) Date of Patent: Aug. 1, 2023

(54) CLEANING SOLVENT COMPOSITIONS EXHIBITING AZEOTROPE-LIKE BEHAVIOR AND THEIR USE

(71) Applicant: Zynon Technologies, LLC, New Britain, CT (US)

(72) Inventor: Venesia L. Hurtubise, Hartford, CT (US)

(73) Assignee: ZYNON TECHNOLOGIES, LLC, New Britain, CT (US)

(*) Notice: Subject to any disclaimer, the term of this patent is extended or adjusted under 35 U.S.C. 154(b) by 225 days.

(21) Appl. No.: 17/401,565

(22) Filed: Aug. 13, 2021

(65) Prior Publication Data

US 2022/0056368 A1    Feb. 24, 2022

Related U.S. Application Data

(60) Provisional application No. 63/067,018, filed on Aug. 18, 2020.

(51) Int. Cl.
  *C11D 7/50*    (2006.01)
  *C11D 1/00*    (2006.01)
  (Continued)

(52) U.S. Cl.
  CPC .............. *C11D 1/004* (2013.01); *C07C 19/08* (2013.01); *C11D 3/3773* (2013.01); *C11D 7/50* (2013.01); *C11D 11/0047* (2013.01)

(58) Field of Classification Search
  CPC ....................................................... C11D 7/50
  (Continued)

(56) References Cited

U.S. PATENT DOCUMENTS 2,999,815 A    9/1961  Eiseman, Jr.
3,776,693 A   12/1973  Smith et al.
(Continued)

FOREIGN PATENT DOCUMENTS

CN    105566074 A      5/2016
CN    113444492 A  *  9/2021
(Continued)

OTHER PUBLICATIONS

"Phosphate Esters", Publication of Lakeland Laboratories Limited, Manchester, England, Ref: Lakeland Phos. Esters (4), 3/00, 12 pages.
(Continued)

*Primary Examiner* — Gregory E Webb
(74) *Attorney, Agent, or Firm* — Cantor Colburn LLP

(57) ABSTRACT

An azeotropic cleaning solvent composition has from about 96 to about 98 weight percent 1,1,1,3,3,3-hexafluoro-2-methoxypropane ("HFMOP") and from about 2 to about 4 weight percent acetone, for example, about 97 weight percent HFMOP and about 3 weight percent acetone. Another composition of the invention has a weight ratio of HFMOP to acetone of about 24 to about 99, for example, about 24 to 49. Conventional additives such as surfactants, lubricants and co-solvents may be present in an amount not to exceed about 10 weight percent of the composition. A method of the invention comprises contacting an article of manufacture with the solvent composition in order to clean the article of manufacture and then removing the solvent composition from the article of manufacture.

13 Claims, 3 Drawing Sheets

(51) Int. Cl.
  *C07C 19/08* (2006.01)
  *C11D 3/37* (2006.01)
  *C11D 11/00* (2006.01)

(58) Field of Classification Search
  USPC .......................................................... 510/177
  See application file for complete search history.

(56) References Cited

U.S. PATENT DOCUMENTS

| | | | |
|---|---|---|---|
| 4,724,096 A | 2/1988 | Figiel et al. | |
| 5,023,009 A | 6/1991 | Merchant | |
| 5,023,010 A | 6/1991 | Merchant | |
| 5,026,498 A | 6/1991 | Merchant | |
| 5,064,559 A | 11/1991 | Merchant et al. | |
| 5,098,595 A | 3/1992 | Merchant | |
| 5,334,325 A | 8/1994 | Chaussee | |
| 5,856,286 A | 1/1999 | Nalewajek et al. | |
| 5,908,822 A | 6/1999 | Dishart | |
| 6,053,952 A | 4/2000 | Kaiser | |
| 6,312,759 B1 | 11/2001 | Yamada et al. | |
| 6,350,395 B1 | 2/2002 | Kuemin | |
| 6,660,709 B1 | 12/2003 | Dournel et al. | |
| 6,848,790 B1 | 1/2005 | Evers et al. | |
| 7,497,877 B2 | 3/2009 | Goedhart et al. | |
| 7,531,496 B2 | 5/2009 | Minor et al. | |
| 7,629,307 B2 | 12/2009 | Owens | |
| 8,066,900 B2 | 11/2011 | Owens | |
| 8,410,039 B2 | 4/2013 | Bartelt et al. | |
| 8,637,443 B2 | 1/2014 | Basu et al. | |
| 9,309,451 B2 | 4/2016 | Nishiguchi et al. | |
| 10,787,632 B2 | 9/2020 | Cunningham et al. | |
| 10,883,071 B2 | 1/2021 | Cunningham et al. | |
| 2004/0117918 A1 | 6/2004 | Scheper et al. | |
| 2004/0259752 A1 | 12/2004 | Degroot et al. | |
| 2006/0052268 A1 | 3/2006 | Artuphel et al. | |
| 2006/0200914 A1 | 9/2006 | Evers et al. | |
| 2006/0217277 A1 | 9/2006 | Lallier et al. | |
| 2007/0010421 A1 | 1/2007 | Wu | |
| 2007/0203045 A1 | 8/2007 | Schweitzer et al. | |
| 2008/0139444 A1 | 6/2008 | Bartelt | |
| 2008/0274935 A1 | 11/2008 | Dingess | |
| 2009/0156861 A1 | 6/2009 | Ohtsuka et al. | |
| 2009/0186799 A1 | 7/2009 | Owens | |
| 2009/0186800 A1 | 7/2009 | Owens | |
| 2012/0122996 A1 | 5/2012 | Basu et al. | |
| 2015/0122461 A1 | 5/2015 | Nishiguchi et al. | |
| 2015/0329806 A1 | 11/2015 | Robin et al. | |
| 2016/0023974 A1 | 1/2016 | Bonnet et al. | |
| 2016/0326458 A1 | 11/2016 | Smets et al. | |
| 2016/0326468 A1 | 11/2016 | Robin et al. | |
| 2017/0283959 A1 | 10/2017 | Shellef et al. | |
| 2018/0216047 A1 | 8/2018 | Cunningham et al. | |
| 2019/0119609 A1 | 4/2019 | Shellef et al. | |
| 2020/0024553 A1 | 1/2020 | Ye | |
| 2020/0181544 A1 | 6/2020 | Cunningham et al. | |

FOREIGN PATENT DOCUMENTS

| | | | |
|---|---|---|---|
| JP | 1139863 A | 6/1989 | |
| JP | 10130183 A | 5/1998 | |
| JP | 2881190 B2 | 4/1999 | |
| JP | 2019167304 A | 10/2019 | |
| WO | 9640834 A1 | 12/1996 | |
| WO | 2012121749 A1 | 9/2012 | |
| WO | 2014147311 A1 | 9/2014 | |

OTHER PUBLICATIONS

International Search Report for International Application No. PCT/US21/46198; International Filing Date Aug. 17, 2021; dated Nov. 30, 2021; 2 pages.

Thesis of Jacob David Perry, "Identification and Characterization of Non-Flammable Azeotropic Mixtures For Precision Cleaning," May 2017, 119 pages.

Written Opinion for International Application No. PCT/US21/46198; International Filing Date Aug. 17, 2021; dated Nov. 30, 2021; 4 pages.

* cited by examiner

CLEANING SOLVENT COMPOSITIONS EXHIBITING AZEOTROPE-LIKE BEHAVIOR AND THEIR USE

CROSS-REFERENCE TO RELATED APPLICATION

This application claims priority of provisional patent application Ser. No. 63/067,018 filed on Aug. 18, 2020 in the name of Venesia L. Hurtubise, and entitled "CLEANING SOLVENT COMPOSITIONS EXHIBITING AZEOTROPE-LIKE BEHAVIOR AND THEIR USE".

BACKGROUND OF THE INVENTION

Field of the Invention

The present invention concerns solvent-based cleaning compositions of the type used in industrial processes for cleaning a wide variety of articles of manufacture including metals and plastics in the metal-working, electronics and other industries.

Description of Related Art

Solvent based cleaning compositions are used in industrial processes for cleaning a wide variety of soiling substances and residues (below sometimes referred to as "soils" or "soiling substances"). The electronics industry typically cleans fluxes, solder pastes, adhesives and coatings from a variety of devices before and after assembly of components. Such devices may comprise one or more of a wide range of materials comprising metal, ceramic and synthetic polymer (plastic) substrates and components. Metal working operations must remove lubricant oils and soaps, grinding media and greases from metal surfaces. Many of these soils are very difficult to strip from metal surfaces, especially with non-aqueous cleaners.

Of special interest are non-flammable blends of solvents that provide a cleaning solvent which can be used safely in aerosol packages, or as wiping fluids or in bulk cleaning tanks, for example, in vapor degreasing ("VDG") units. Typically, these cleaning solvents comprise halogenated compounds that are either non-flammable themselves or can be rendered non-flammable in a mixture with other halogenated compounds. For example, it is known to use chlorinated hydrocarbons, such as flammable trans-dichloroethylene (TDCE), as the high solvency component with fluorinated components that serve to render the cleaning solvent blend non-flammable. In addition, and especially for VDG applications, the cleaning solvent blend should be an azeotrope or an azeotrope-like composition that is non-flammable so that the vapor is also non-flammable. Therefore, it is highly desirable that the azeotrope not significantly fractionate after distillation, condensation and re-mixing, as happens in a vapor degreaser. That is, the component ratios should be nearly the same in the boil sump as in the rinse sump in a VDG, or in the boil flask and receiver over the course of a full distillation.

The industry seeks to maximize the cleaning power of its products, often defined as the Kauri-Butanol index ("KB value"). To do this, the concentration of a high KB value component in the blend is made as high as is feasible. However, the solvent blend becomes more difficult to render non-flammable as the amount of the high KB value component in the composition is increased. A significant advance in the art was made by Dupont Corporation with the introduction of an azeotrope-like blend of 4% by weight methyl perfluoroheptene (MPHE) ethers, 0.8% Vertrel XF and 95.2% TDCE, offered as Vertrel Sion. This is currently the highest concentration of TDCE in a commercial product. However, the high TDCE concentration adversely affects flammability, that is, the Vertrel Sion solvent may be more flammable than desired.

Japanese Patent application JPH10130183(A) ("Yuji et al.") discloses azeotropic compositions useful for cleaning electronic parts or the like, one embodiment of the disclosed compositions being comprised of blends of 55 to 75 weight percent 1,1,1,3,3,3,-hexafluoro-2-methoxypropane ether (HFMOP") and 25 to 45 weight percent acetone. As shown by the flammability test of Part A of Example 2 below, the Yuji et al. composition containing 75 weight percent HFMOP and 25 weight percent acetone is highly flammable. Increased amounts of acetone above 25 weight percent and up to 45 weight percent as taught by Yuji et al. would further increase flammability. Other solvent cleaning compositions disclosed in Yuji et al. combine HFMOP with cyclohexane, hexane or cyclopentane. The HFMOP/cyclohexane composition of Yuji et al. discloses 75 to 95 weight percent HFMOP.

Patent publication US 2020/0024553 A1 of Zhihung Ye was published on Jan. 23, 2020 and discloses an azeotropic composition comprising a blend of 1,1,1,3,3,3,-hexafluoro-2-methoxypropane and a second component selected from the group consisting of isopropyl alcohol, ethanol, methanol, and trans-1,2-dichloroethylene. The azeotropic composition is said to exhibit a substantially constant boiling point at a constant pressure and to be useful for various cleaning and degreasing applications.

U.S. Pat. No. 7,531,496 B2 to B. H. Minor et al. issued on May 12, 2009 discloses binary azeotrope-like compositions consisting essentially of 1,1,1,3,3-pentafluorobutane (HFC-365mfc) and 1,1,1,2,3,4,4,5,5,5-decafluoropentane (HFC-43-10mee) or nonafluoromethoxybutane. Also disclosed are ternary or quaternary azeotrope-like compositions consisting essentially of 1,1,1,3,3-pentafluorobutane and 1,1,1,2,3,4,4,5,5,5-decafluoropentane or nonafluoromethoxybutane, and additionally trans-1,2-dichloroethylene, n-propyl bromide, acetone, methanol, ethanol or isopropanol.

U.S. Pat. No. 5,064,559 to A. B. Merchant et al. issued on Nov. 12, 1991 and discloses a cleaning solvent comprising azeotropic mixtures of 1,1,1,2,3,4,4,5,5,5-decafluoropentane and methanol or ethanol or isopropanol, the azeotropic mixtures being useful in solvent cleaning applications, as blowing agents, refrigerants, heating mediums and aerosol propellants.

U.S. Pat. No. 8,410,039 to J. E. Bartelt et. al. issued on Apr. 2, 2013 discloses blends and uses of azeotropic formulations of methyl perfluoroheptene ethers and trans-dichloroethylene.

U.S. Pat. No. 6,312,759 to T. Yamada et. al. issued on Nov. 6, 2001 discloses blends of 95% or more heptafluorocyclopentane (HFCP) with many other solvents to be used as cleaning compositions or carrier fluids.

SUMMARY OF THE INVENTION

Generally, the present invention concerns low flammability cleaning solvent compositions exhibiting azeotrope-like behavior, for example in vapor degreaser operations, and the use of such cleaning solvents. Furthermore the cleaning solvent compositions of the present invention are essentially non-fractionating upon distillation, which is important for both the efficient and safe operation of cleaning operations and safety of various solvent packages such as bulk solvent, and solvent aerosol, wipes, and pump sprays. The cleaning solvent compositions of the present invention comprise blends of 1,1,1,3,3,3-hexafluoro-2-methoxypropane ("HFMOP") ether and acetone. HFMOP is a fluoroether having the following structure

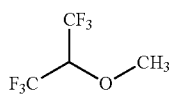

and the following characteristics.

| Molecular wt: | 182 | Viscosity: | 0.33 cSt (at 25° C.) |
|---|---|---|---|
| Boiling Point: | 50° C. | Density: | 1.39 g/mL (at 25° C.) |
| Freezing Point: | <−78° C. | KB Value: | 12.2 |
| Flash Point: | Not Detectable | | |

Specifically, in accordance with one aspect of the present invention there is provided a solvent composition having azeotrope-like properties and comprising 1,1,1,3,3,3-hexafluoro-2-methoxypropane ether ("HFMOP") and acetone, the HFMOP and the acetone being present in a weight ratio of about 24 to about 99, for example, about 24 to about 49, parts HFMOP, to one part acetone, for example, in a weight ratio of HFMOP to acetone of from about 27.9 to 39.0.

Other aspects of the present invention provide that the composition further optionally comprises one or more additives which do not significantly adversely affect the azeotrope-like and non-flammable properties of the composition of the present invention and, if present, are present in a limited amount not exceeding about 10 weight percent of the composition.

Such additives, when present, are selected from the class consisting of one or more of surfactants, lubricants and co-solvents conventionally used in cleaning solvent compositions. In related aspects of the present invention the surfactants, when present, are selected from the class consisting of one or more of alkyl phosphate amine salts, ethoxylated alcohols, and quaternary ammonium salts; the lubricants, when present, are selected from one or more of mineral oil, alkyl benzenes, polyol esters, and fluorinated lubricants including perfluoropolyethers, fluorosilicones, polytetrafluoroethylene, and polytrifluorochloroethylenes; and the co-solvents, when present, are selected from the class consisting of one or more of alcohols such as methanol, ethanol, n-propanol, isopropanol and benzyl alcohol, esters, ethers, ether alcohols and hydrocarbons such as pentane, cyclopentane, hexane, cyclohexane, heptane and octane.

Another aspect of the present invention provides for a solvent composition having azeotrope-like properties and comprising from about 96 to about 99 weight percent 1,1,1,3,3,3-hexafluoro-2-methoxypropane ether ("HFMOP") and from about 1 to about 4 weight percent acetone, or from about 96 to about 98 weight percent HFMOP and from about 2 to about 4 weight percent acetone. In related aspects, acetone comprises from about 2.0 to about 3.5 weight percent of the composition, for example, acetone may comprise from about 2.5 to about 3 or about 3.5 weight percent of the composition, with HFMOP comprising from about 96.5 to about 98 weight percent of the composition. Additives may optionally be present in the composition of the present invention, or the composition may comprise substantially only HFMOP and acetone, except for trace impurities which may be found in commercially available HFMOP and acetone.

In accordance with a method aspect of the present invention, there is provided a method of cleaning an article of manufacture by contacting the article with a solvent composition having azeotrope-like properties and comprising 1,1,1,3,3,3-hexafluoro-2-methoxypropane ether ("HFMOP") and acetone, the HFMOP and the acetone being present in a weight ratio of from about 24 to about 99 parts HFMOP to about 1 part acetone, or about 24 to about 49 parts HFMOP to about one part acetone, for example, in a weight ratio of HFMOP to acetone of from about 27.6 to about 39.0, and the composition optionally further comprises one or more additives which do not adversely affect the azeotrope-like and non-flammable properties of the composition and, if present, are present in an amount not exceeding about 10 weight percent of the composition. The additives, when present, are those surfactants, lubricants and co-solvents described above. The solvent composition is removed from the article after the contacting of the article with the solvent composition.

A further method aspect of the present invention provides that the composition is vaporized and the article is contacted with the resulting vapor, and after such contacting the vapor is condensed to the liquid composition.

Other aspects of the present invention will be apparent from the following detailed description.

Unless otherwise specifically stated, all percentages of a given component, whether expressed as "weight percent", "%", "wt %" or otherwise, are percent by weight of the component in the solvent composition, based on the total weight of the composition.

As used herein, the term "azeotrope-like" behavior or characteristics or language of similar import used with reference to the cleaning solvent blends of the present invention means that while the solvent blends may not exhibit perfect azeotropic characteristics (although some of the blends of the present invention may do so), the changes in composition after repeated distillation cycles are small. As a practical matter, a change of not more than 20 wt percent of the starting amount of a major component of a solvent blend composition is often considered acceptable. As demonstrated in Example 1 below, the change after seven hours of distillation in the starting amount of HFMOP in a 3 wt percent acetone embodiment of the present invention is quite small. Such change is preferably less than 10 wt percent, more preferably less than 5 wt percent of the starting content of HFMOP, e.g., not more than about 2 wt percent.

DETAILED DESCRIPTION OF THE INVENTION AND SPECIFIC EMBODIMENTS THEREOF

Figure 1:
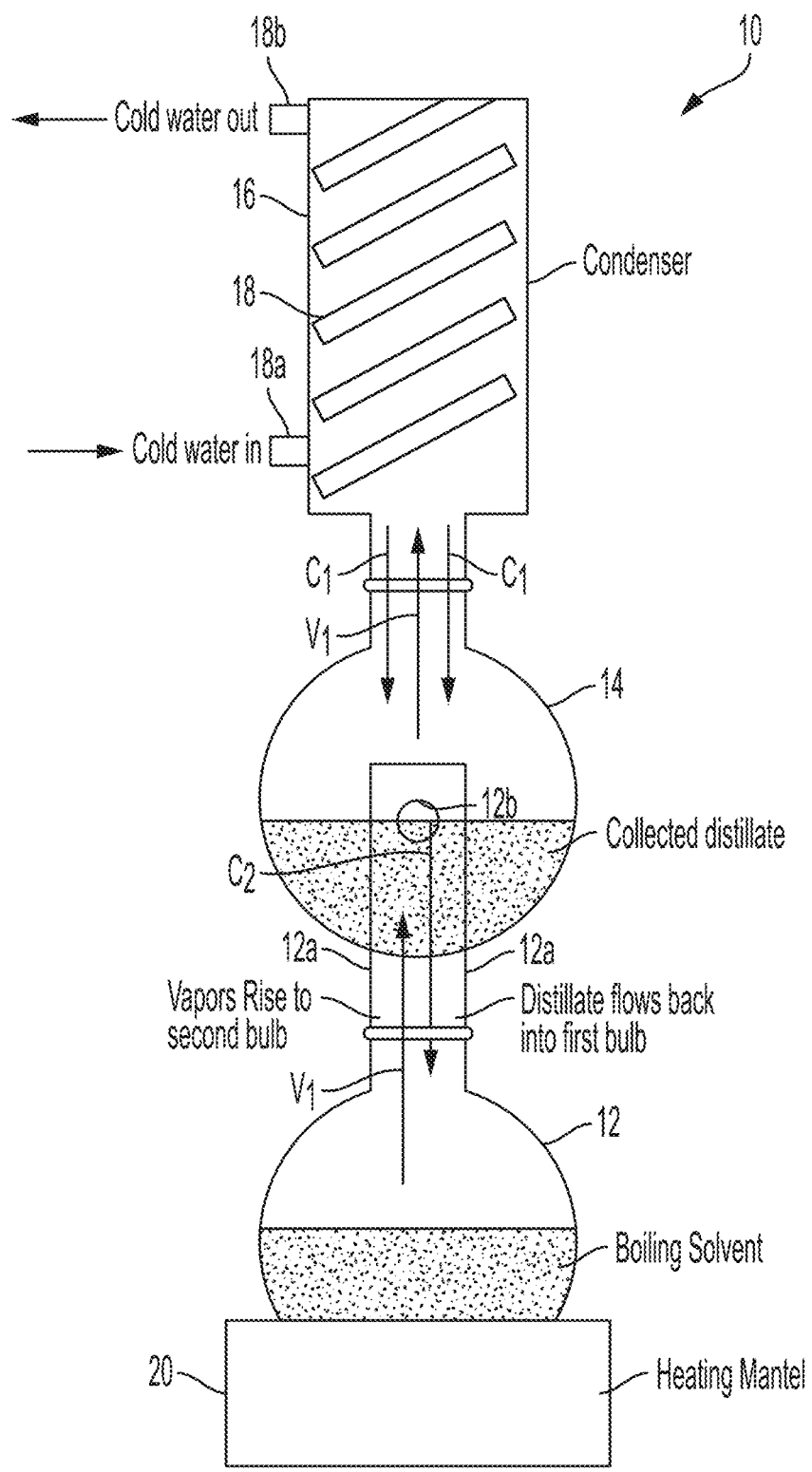
FIG. 1 is a schematic view in elevation of a bench top simulation of a standard 2-sump vapor degreaser comprising a "dual bulb" apparatus of the type used to develop the data illustrated in FIGS. 2-5.

FIG. 1 schematically illustrates a conventional dual-bulb bench top laboratory glassware of the type utilized to simulate operation of a VDG unit and generate the data presented below. Laboratory glassware 10 comprises a boil bulb 12 having a neck 12a which protrudes into rinse bulb 14. Neck 12a has formed therein an aperture 12b which is disposed within rinse bulb 14. A condenser 16 is fitted to rinse bulb 14 at the outlet end thereof and comprises a cooling coil 18 disposed within condenser 16. A cold water inlet 18a is connected to a source of cooling water (not shown) and a cold water outlet 18b is connected to a water discharge (not shown). Boil bulb 12 is disposed upon a heating mantel 20.

In use, a solvent composition to be tested is introduced into boil bulb 12 and heated to boil the solvent composition and generate a vapor which rises to rinse bulb 14 and then into condenser 16 as indicated by arrows $V_1$. Vapor is condensed by contact with cooling coil 18 and flows into rinse bulb 14 as indicated by arrows $C_1$. When the condensate collected in rinse bulb 14 reaches the level of aperture 12b, the overflow solvent flows back into boil bulb 12 as indicated by arrow $C_2$.

Standard Test Procedure. Trials were conducted in a bench top simulation of a standard 2-sump vapor degreaser using a "dual bulb" apparatus of the type illustrated in FIG. 1, having a sampling port (not shown in FIG. 1) on the boil flask. Samples from various locations and times are analyzed by gas chromatography using an Agilent Corporation DB-200 capillary column (trifluoropropyl methyl dimethyl siloxane stationary phase) and an FID detector. The following Examples report the results of trials conducted pursuant to this Standard Test Procedure.

Example 1

Formulation of an embodiment (designated 17-90-1) of the present invention containing 97 wt percent HFMOP and 3 wt percent acetone is distilled in laboratory glassware of the type schematically illustrated in FIG. 1.

| Part A-Change in Boil Composition by Distillation in Laboratory Glassware Simulating a Vapor Degreaser Prototype 17-90-1 Vapor Degreaser Simulation | | |
|---|---|---|
| Total Time Distilled (hours) | wt % HFMOP | wt % ACETONE |
| 0 | 97.00 | 3.00 |
| 1 | 95.45 | 4.55 |
| 2 | 95.57 | 4.43 |
| 3 | 95.59 | 4.41 |
| 4 | 95.62 | 4.38 |
| 5 | 95.60 | 4.40 |
| 6 | 95.58 | 4.42 |
| 7 | 95.58 | 4.42 |

The change in HFMOP starting content is 97.00−95.58=1.42. This represents a reduction of HFMOP in the boil composition over the course of seven hours of distillation of 1.42/97.00=1.46 wt %.

| Part B-Change in Rinse Composition by Distillation in Laboratory Glassware Simulating a Vapor Degreaser Prototype 17-90-1 Vapor Degreaser Simulation | | |
|---|---|---|
| Total Time Distilled (hours) | wt % HFMOP | wt % ACETONE |
| 0 | 97.00 | 3.00 |
| 1 | 98.24 | 1.76 |
| 2 | 98.09 | 1.91 |
| 3 | 98.02 | 1.98 |
| 4 | 97.98 | 2.02 |
| 5 | 97.96 | 2.04 |
| 6 | 97.93 | 2.07 |
| 7 | 97.90 | 2.10 |

The change in HFMOP content in the rinse composition over the seven hours of distillation, calculated as for the boil composition, is an increase of 0.90/97.00=0.93 wt %.

As the above data shows, Prototype 17-90-1 exhibits azeotropic properties. The boiling point of Prototype 17-90-1 was determined to be 51.3° C., which is 4.5° C. lower than the calculated boiling point. The distillation data indicate that the composition does shift initially from 3 wt % acetone to 2 wt % in the rinse and 4 wt % in the boiling areas of the system. The 7-hour distillation evaluation depicts the stability of the blend after the initial shift.

Figure 2:
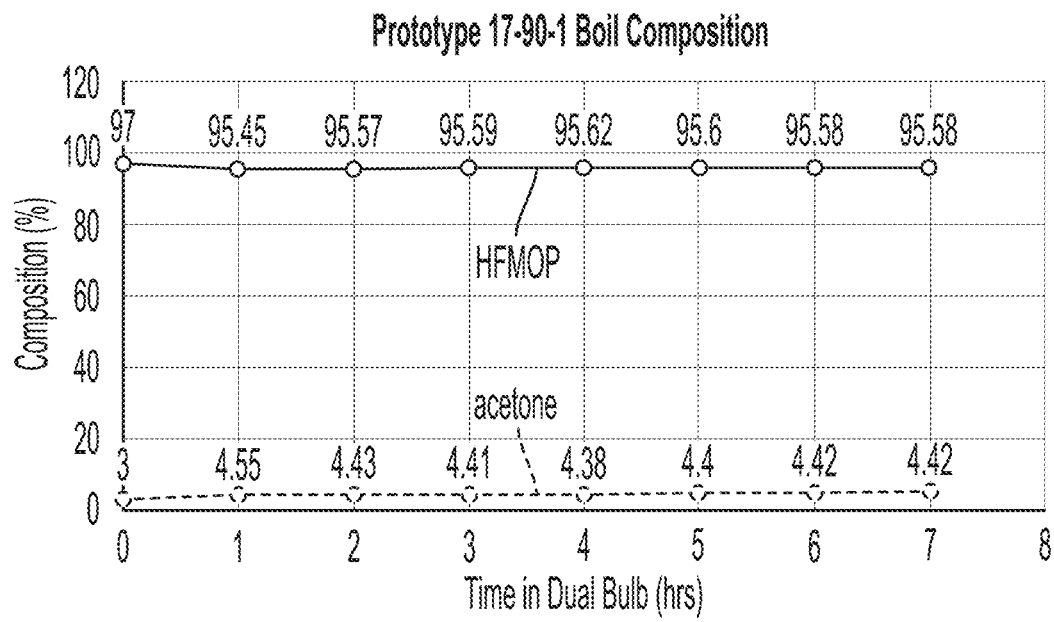
FIG. 2 is a graph plotting the change in composition of the HFMOP and acetone components of a cleaning solvent embodiment of the present invention over seven hours of operation measured in the boil sump of the apparatus of FIG. 1.
Figure 3:
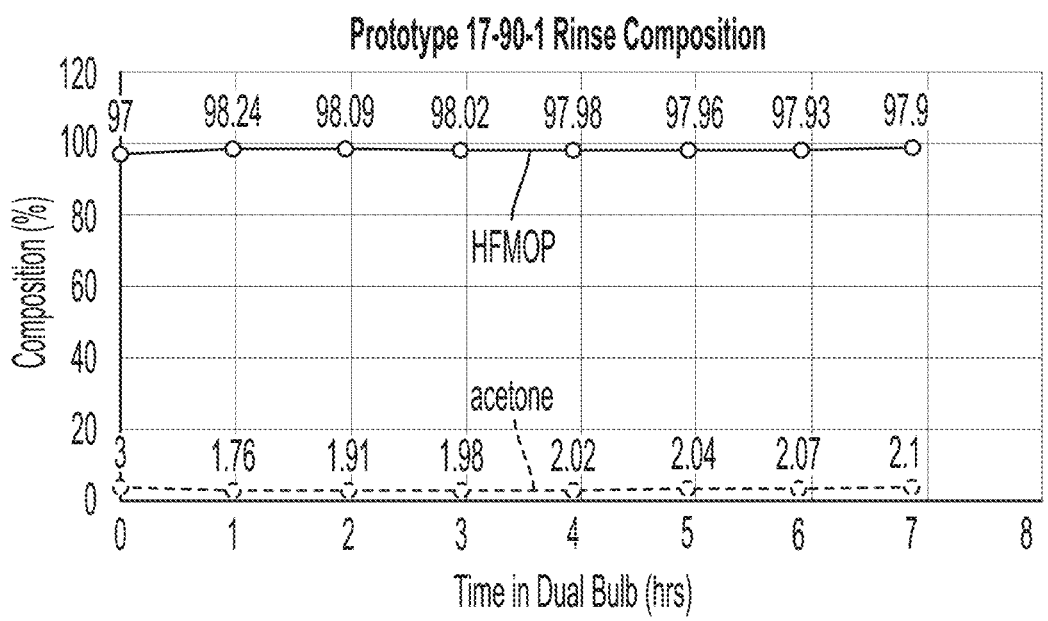
FIG. 3 is a graph identical to that of FIG. 2 except that it shows the change in composition in the rinse sump of the dual bulb apparatus.
Figure 4:
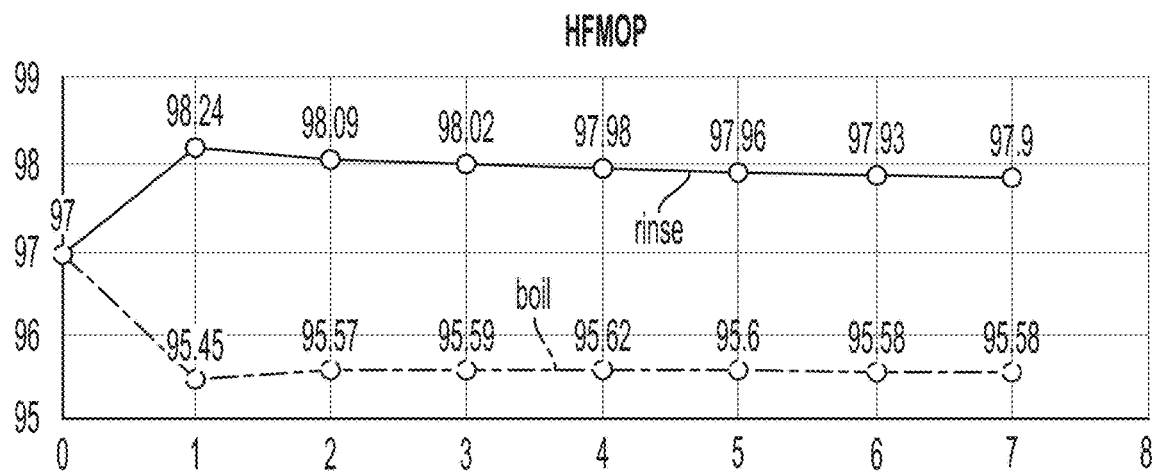
FIG. 4 is a graph plotting the data of FIGS. 2 and 3 against the time of operation of the apparatus, but showing the change in quantity of the HFMOP component in the boil and rinse sumps.
Figure 5:
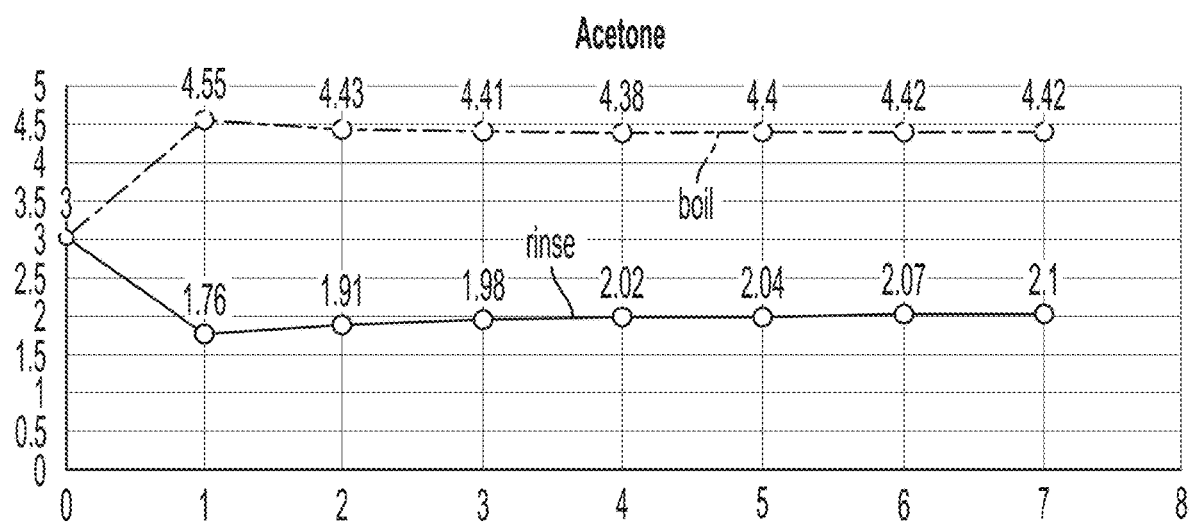
FIG. 5 is a graph identical to that of FIG. 4 except that it plots the change in quantity of the acetone component.

Example 1 demonstrates that only a limited change in the initially present quantity of each component of the blend is sustained in the boil and rinse sumps after an evaporation and condensation period of seven hours in the apparatus of FIG. 1 as is shown in FIGS. 2 and 3. FIGS. 4 and 5 show the changes in composition in the boil and rinse sumps of the apparatus of FIG. 1 for, respectively, HFMOP and acetone.

HFMOP in combination with acetone in the stated proportions has been found to provide an advantageous alternative to known compositions containing other hydrofluoroethers ("HFEs") in combination with a high KB flammable solvent. A major benefit of using HFEs instead of hydrofluorocarbons ("HFCs") in cleaning solvents is improved environmental characteristics. HFMOP has shown flammability suppression characteristics which allow it to be blended with flammable solvents having a high KB value, such as acetone, to provide non-flammable compositions. It is of course highly desirable to form non-flammable azeotropes with the HFE and flammable cleaning solvents.

The following compositions were tested by a "pan test" for flammability. A metal pan was filled with 10 mL of solvent in a fume hood. A flame source was passed over the surface of the liquid and the flame was monitored for size and duration. Once the flame extinguished, the fumes were allowed to dissipate for 30 seconds. The flame source was then passed over the solvent surface again. This process was repeated until all of the solvent had evaporated. The testing was ceased if the flames did not self-extinguish within 10 seconds. A solvent which self-extinguished the flames in less than 5 seconds was deemed "non-flammable." A solvent which did not extinguish the flames after 5 seconds was deemed "flammable." This test method is a procedure employed to gauge flammability potential for solvent blends before testing via closed-cup or open-cup methods.

Example 2

Each composition comprised the stated weight % of solvent, balance HFMOP.

| Part A-Comparative Examples | |
|---|---|
| Composition | Flammability Results |
| HFMOP and Ethanol | |
| 3 wt % ethanol | flammable |
| 5 wt % ethanol | flammable |
| HFMOP and Trans-dichloroethylene ("Trans") | |
| 50 wt % trans | non-flammable |
| 80 wt % trans | flammable |
| 95 wt % trans | flammable |
| HFMOP and Isopropyl Alcohol (IPA") | |
| 3 wt % IPA | flammable |
| HFMOP and Acetone (Example taken from Yuji et al. JPH 10130183A, noted above) | |
| 25 wt % acetone | highly flammable |

| Part B-Embodiments of the Present Invention | |
|---|---|
| Composition | Flammability Results |
| HFMOP and acetone | |
| 1 wt % acetone | non-flammable |
| 2 wt % acetone | non-flammable |
| 2.5 wt % acetone | non-flammable |
| 3 wt % acetone (Prototype 17-90-1) | non-flammable |
| 4 wt % acetone | non-flammable |

The flammability tests of Example 2 demonstrate that blends of HFMOP or other HFEs with certain alcohols or trans-dichloroethylene as taught in the prior art are flammable. In contrast, Prototype 17-90-1, a blend of HFMOP with acetone (3 wt % acetone) is self-extinguishing. Further, flammability studies of Prototype 17-90-1 indicate that the blend does not become flammable over time. A low acetone content less than one percent is of course non-flammable but results in poor cleaning power.

The present invention has been described in detail with respect to specific embodiments thereof but these specific embodiments are not intended to be construed as limitations on the scope of the invention.

What is claimed is:

1. A solvent composition having azeotrope-like properties and comprising 1,1,1,3,3,3-hexafluoro-2-methoxypropane ether ("HFMOP") and acetone, the HFMOP and the acetone being present in a weight ratio of about 24 to about 99 parts HFMOP to one part acetone.

2. The composition of claim 1 wherein the HFMOP and the acetone are present in a weight ratio of about 24 to about 49 parts HFMOP to one part acetone.

3. The composition of claim 1 or claim 2 further comprising one or more additives which do not adversely affect the azeotropic-like properties of the composition and, if present, are present in an amount not exceeding about 10 weight percent of the composition.

4. The composition of claim 3 wherein the additives, when present, are selected from the class consisting of one or more of surfactants, lubricants and co-solvents.

5. The composition of claim 3 wherein the surfactants, when present, are selected from the class consisting of one or more of alkylphosphate amine salts, ethoxylated alcohols, and quaternary ammonium salts; the lubricants, when present, are selected from one or more of mineral oil, alkyl benzenes, polyol esters, perfluoropolyethers, fluorosilicones, polytetrafluoroethylene, and polytrifluorochloroethylenes; and the co-solvents, when present, are selected from the class consisting of one or more of methanol, ethanol, n-propanol, isopropanol, benzyl alcohol, esters, ethers, ether alcohols, pentane, cyclopentane, hexane, cyclohexane, heptane and octane.

6. The composition of claim 3 wherein the HFMOP and acetone are present in a weight ratio of from about 27.6 to about 39.0 parts HFMOP to one part acetone.

7. A solvent composition having azeotrope-like properties and comprising from about 96 to about 99 weight percent 1,1,1,3,3,3-hexafluoro-2-methoxypropane ether ("HFMOP") and from about 1 to about 4 weight percent acetone.

8. The composition of claim 7 comprising from about 96 to about 98 weight percent 1,1,1,3,3,3-hexafluoro-2-methoxypropane ether ("HFMOP") and from about 2 to about 4 weight percent acetone.

9. The composition of claim 7 wherein acetone comprises from about 2.5 to about 3.5 weight percent of the composition.

10. The composition of claim 7 wherein acetone comprises from about 2 to about 3 weight percent of the composition.

11. A method of cleaning an article of manufacture by contacting the article with a solvent composition having azeotrope-like properties and comprising 1,1,1,3,3,3-hexafluoro-2-methoxypropane ether ("HFMOP") and acetone, the HFMOP and the acetone being present in a weight ratio of from about 24 to about 99 parts HFMOP to one part acetone, and the composition optionally further comprising, one or more additives which do not adversely affect the azeotrope-like properties of the composition and, if present, are present in an amount not exceeding about 10 weight percent of the composition, the additives, when present, being selected from the class consisting of one or more surfactants selected from one or more of alkylphosphate amine salts, ethoxylated alcohols, and quaternary ammonium salts; the lubricants, when present, being selected from one or more of mineral oil, alkyl benzenes, polyol esters, perfluoropolyethers, fluorosilicones, polytetrafluoroethylene, and polytrifluorochloroethylenes; and the co-solvents, when present, are selected from the class consisting of one or more of methanol, ethanol, n-propanol, isopropanol, benzyl alcohol, esters, ethers, ether alcohols, pentane, cyclopentane, hexane, cyclohexane, heptane and octane and removing the solvent composition from the article after the contacting of the article with the solvent composition.

12. The method of claim 11 wherein the HFMOP and the acetone are present in a weight ratio of from about 24 to about 49 parts HFMOP to one part acetone.

13. The method of claim 11 or claim 12 wherein the composition is vaporized and the article is contacted with the resulting vapor, and after such contacting the vapor is condensed to the liquid composition.

* * * * *